United States Patent
Ma et al.

(10) Patent No.: US 9,259,554 B2
(45) Date of Patent: Feb. 16, 2016

(54) SYSTEMS AND METHODS TO COMPENSATE FOR COMPRESSION FORCES IN AN INTRAVASCULAR DEVICE

(75) Inventors: Yiping Ma, Layton, UT (US); Marty L. Stout, South Jordan, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 626 days.

(21) Appl. No.: 13/042,127

(22) Filed: Mar. 7, 2011

(65) Prior Publication Data

US 2012/0232498 A1    Sep. 13, 2012

(51) Int. Cl.
*A61M 25/06*    (2006.01)
*A61M 39/24*    (2006.01)
*A61M 39/00*    (2006.01)

(52) U.S. Cl.
CPC ....... *A61M 25/0693* (2013.01); *A61M 25/0606* (2013.01); *A61M 39/24* (2013.01); *A61M 2039/0063* (2013.01); *A61M 2039/0072* (2013.01); *A61M 2039/2426* (2013.01); *A61M 2207/00* (2013.01)

(58) Field of Classification Search
CPC ..................... A61M 25/0693; A61M 25/0606; A61M 39/24; A61M 2039/0063; A61M 2039/0072; A61M 2039/2426; A61M 2207/00
USPC ................... 604/167.01–167.06, 256, 168.01
See application file for complete search history.

(56) References Cited

U.S. PATENT DOCUMENTS

| | | |
|---|---|---|
| 4,387,879 A | 6/1983 | Tauschinski |
| 4,449,693 A | 5/1984 | Gereg |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,295,969 A | 3/1994 | Fischell et al. |
| 5,330,435 A | 7/1994 | Vaillancourt |

(Continued)

FOREIGN PATENT DOCUMENTS

| | | |
|---|---|---|
| CA | 2133053 A1 | 3/1995 |
| WO | WO 99/34849 | 7/1999 |
| WO | WO 2006/037638 A1 | 4/2006 |

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Emily Schmidt
*Assistant Examiner* — Lauren M Peng
(74) *Attorney, Agent, or Firm* — Jeanne Lukasavage; Craig Metcalf; Kirton McConkie

(57) ABSTRACT

A system and method for providing vent channel geometries to compensate for compression forces experienced by a septum within an intravascular device.

10 Claims, 13 Drawing Sheets

(56) References Cited

U.S. PATENT DOCUMENTS

| | | |
|---|---|---|
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A * | 1/1996 | Vaillancourt ............ 604/86 |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A * | 5/1998 | Guala et al. ............ 604/249 |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,396,348 B2 * | 7/2008 | Newton et al. ............ 604/256 |
| 7,470,254 B2 | 12/2008 | Basta et al. |
| 7,736,339 B2 | 6/2010 | Woehr et al. |
| 7,914,494 B2 | 3/2011 | Hiejima |
| 2007/0083157 A1 | 4/2007 | Belley et al. |
| 2007/0083162 A1 | 4/2007 | O'Reagan et al. |
| 2007/0233007 A1* | 10/2007 | Adams ............ A61M 25/0097 604/168.01 |
| 2008/0039796 A1 | 2/2008 | Nakajima |
| 2008/0108944 A1 | 5/2008 | Woehr et al. |
| 2010/0204648 A1* | 8/2010 | Stout et al. ............ 604/122 |
| 2010/0204675 A1 | 8/2010 | Woehr et al. |

\* cited by examiner

SYSTEMS AND METHODS TO COMPENSATE FOR COMPRESSION FORCES IN AN INTRAVASCULAR DEVICE

BACKGROUND OF THE INVENTION

Catheters are commonly used for a variety of infusion therapies. For example, catheters are used for infusing fluids, such as normal saline solution, various medicaments, and total parenteral nutrition into a patient; withdrawing blood from a patient; or monitoring various parameters of the patient's vascular system. Catheters are typically coupled to a catheter adapter that supports catheter and provides for an attachment to IV tubing. Generally, following placement of the catheter into the vasculature of a patient, the catheter adapter may be coupled to a fluid source via a section of IV tubing to infuse fluids into the patient.

In order to verify proper placement of the catheter in the blood vessel, the clinician generally confirms that there is a "flashback" of blood from the patient's vasculature into a flashback chamber of the catheter or catheter adapter. Once proper placement of the catheter is confirmed, the clinician must attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the catheter into the vein of the patient. While this method may prevent undesirable exposure to blood, positive pressure from the IV tubing into the catheter can does not permit desirable flashback and thus reduces a clinician's ability to confirm proper catheter placement.

Accordingly, there is a need in the art for a catheter assembly that permits controlled, desirable flashback without the risk of encountering undesirable exposure to blood. Such a catheter assembly is disclosed herein.

BRIEF SUMMARY OF THE INVENTION

In order to overcome the limitations discussed above, the present invention relates to systems and methods for venting a septum within a catheter device. In particular, the present invention relates to providing various vent geometries to compensate for compression forces experienced by the septum in an assembled intravascular device.

In some implementations, a compression compensating septum device is provided having a proximal end, a distal end and an outer surface, wherein a distal portion of the outer surface is chamfered, such that when the septum device is compression fitted within an intravascular device, a vent is provided between the chamfered portion and the inner surface of the intravascular device. In some instances, an opening of the vent includes a surface area configured to permit or prevent passage of a fluid between a proximal chamber and a distal chamber of the intravascular device. Further, in some implementations an outer surface of the septum includes a plurality of recesses which form vents for the intravascular device. In other implementations, an inner surface of the intravascular device includes a plurality of recesses which form vents for the intravascular device.

In some implementations, a method for venting a septum positioned within a catheter adapter of intravascular device, is provided. In particular, in some implementations a method of venting includes the steps of providing a catheter adapter having an inner surface; positioning a septum within the inner surface of the catheter adapter; providing a vent between an outer surface of the septum and the inner surface of the catheter adapter, the vent having a proximal opening and a distal opening; and chamfering a distal end of the vent to increase a surface area of the distal opening. In some implementations, the method further includes providing vent geometries such that following assembly of the intravascular device, a surface area of the vent's proximal opening is approximately equal to a surface area of the vent's distal opening.

Still further, in some implementations an intravascular device is provided which includes a catheter adapter having an inner surface, a septum being positioned within the inner surface such that the septum divides the inner surface into a proximal chamber and a distal chamber, a vent being provided between an outer surface of the septum and an inner surface of the catheter adapter, the vent having a proximal opening and a distal opening to provide fluid communication between the proximal chamber and the distal chamber, and a compression relief forming a portion of the distal opening of the vent, wherein a surface of the distal opening is approximately equal to a surface area of the proximal opening. In some implementations, the compression relief further includes at least one of a chamfered outer surface of the distal end of the septum, and a chamfered inner surface of the distal end of the inner surface.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

Embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

DETAILED DESCRIPTION OF THE INVENTION

Figure 1:
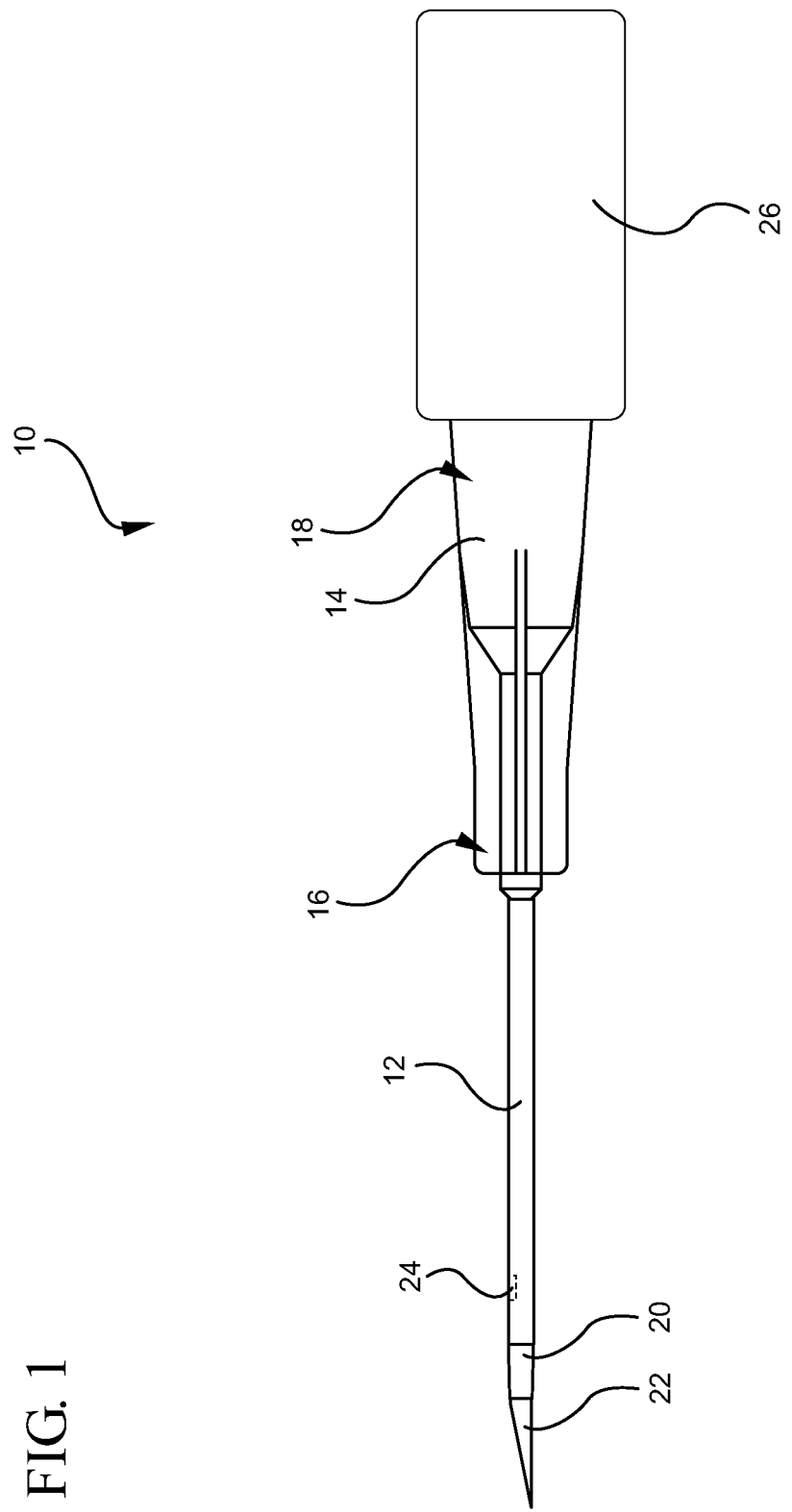
FIG. 1 is a perspective view of an intravascular device in accordance with a representative embodiment of the present invention.

Referring now to FIG. 1, an intravascular device 10 is illustrated. The intravascular device 10 generally includes a catheter 12 coupled to a distal end 16 of a catheter adapter 14. The catheter 12 and the catheter adapter 14 are integrally coupled such that an inner lumen of the catheter adapter 14 is in fluid communication with an inner lumen of the catheter 12. The catheter 12 generally comprises a biocompatible material having sufficient rigidity to withstand pressures associated with insertion of the catheter into a patient.

In some embodiments, as shown, the catheter 12 is an over-the-needle catheter that is made of a flexible or semi-flexible polymer material and which may be used in combination with a rigid introducer needle 22. The rigid introducer needle 22 enables the insertion of the non-rigid over-the-needle catheter into a patient. The introducer needle 22 can be coupled to a needle hub 26 that is selectively coupled to the proximal end 18 of the catheter adapter 14. The introducer needle 22 is typically inserted through the catheter 12 such that a tip of the needle 22 extends beyond the tapered tip 20 of the catheter 12. Insertion of the introducer needle 22 into the vein of the patient creates an opening in the vein through which the tapered tip 20 of the catheter 12 is inserted. The outer surface of the tapered tip 20 enables gradual insertion of the catheter 12 into the opening.

In other embodiments, the catheter 12 is not an over-the-needle catheter, but comprises a rigid, polymer material, such as vinyl. Rigid catheters can include a beveled cutting surface that is utilized to provide an opening in a patient to permit insertion of the catheter 12 into the vascular system of the patient. Accordingly, in some embodiments, the catheter 12 comprises a metallic material, such as titanium, stainless steel, nickel, molybdenum, surgical steel, and alloys thereof. Still, in other embodiments, surgically implanted catheters may also be used in combination with the present invention.

In some embodiments, catheter 12 is a peripheral-type intravenous catheter that generally comprises a short or truncated catheter for insertion into a small peripheral vein. Such catheters generally comprise a diameter of about a 14-gauge catheter or smaller (on a Stubs scale), and are between about 13 mm to 52 mm in length. Peripheral intravenous catheters are typically designed for temporary placement. The short length of the catheter facilitates convenient placement of the catheter. In other embodiments, catheter 12 is a midline or central catheter, which may be longer and used for more extended periods.

Figure 2:
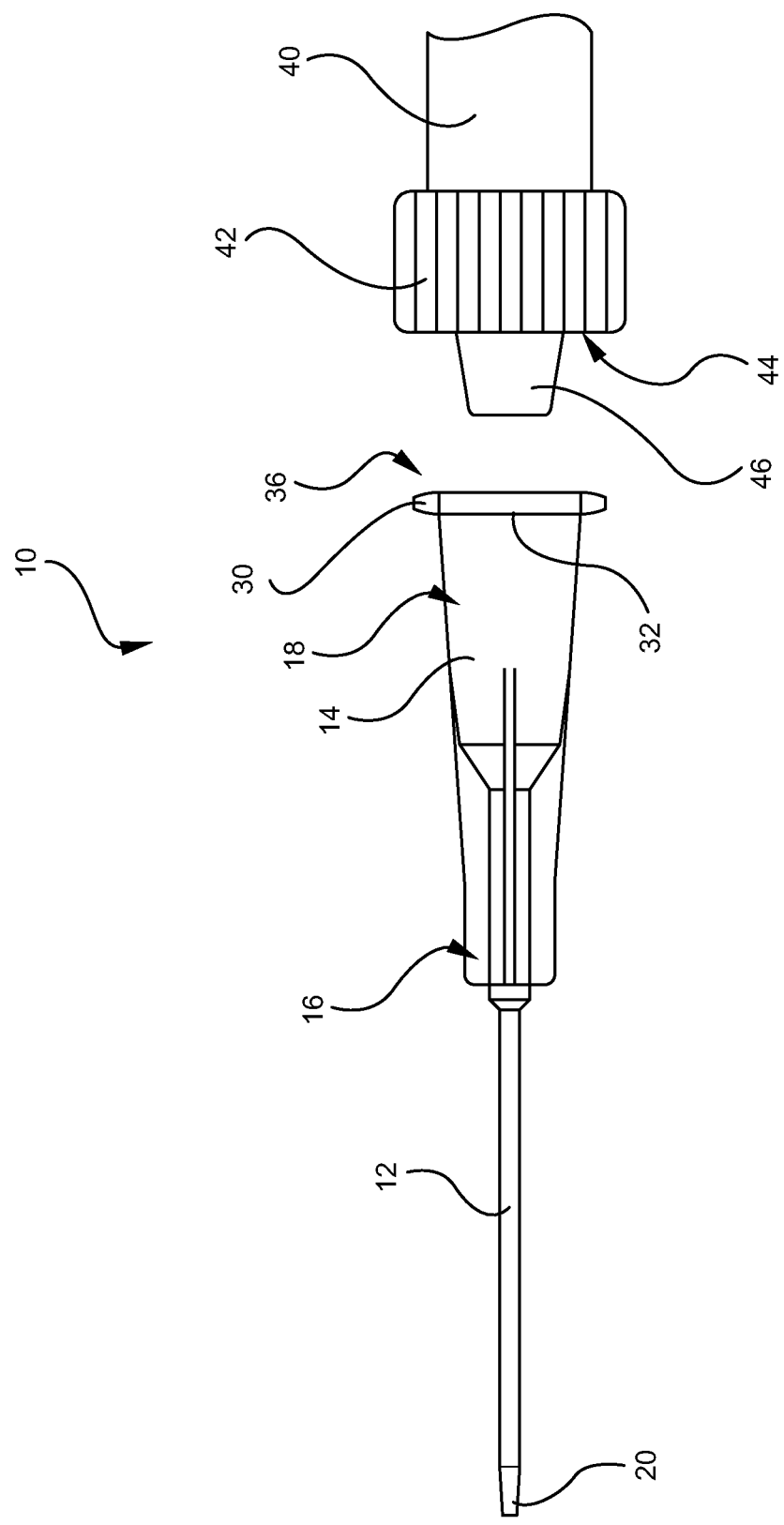
FIG. 2 is a perspective view of an intravascular device following removal of an introducer needle in accordance with a representative embodiment of the present invention.

Referring now to FIG. 2, once catheter 12 is inserted into the vein of the patient, the introducer needle 22 is removed proximally from catheter 12 to provide a fluid conduit through the interior lumen 36 of catheter 12, which can be connected to a fluid source. In some embodiments, a portion of catheter 12 and/or catheter adapter 14 is configured to be connected to a section of intravenous tubing 40 to further facilitate delivery of a fluid to, or removal of a fluid from a patient.

In some embodiments, a proximal end 18 of catheter adapter 14 further includes a flange 32. Flange 32 provides a positive surface which may be configured to enable coupling of an intravenous tubing 40 or patient conduit to the catheter assembly 10. In some embodiments, the flange 32 includes a set of threads 30. The threads 30 are generally provided and configured to compatibly receive a complementary set of threads 44 comprising a portion of a male luer or conduit coupler 42. Conduit coupler 42 is generally coupled to an end portion of the patient conduit 40 in a fluid-tight manner. In some embodiments, an inner portion of conduit coupler 42 is extended outwardly to provide a probe member 46.

In some embodiments, probe member 46 is compatibly inserted within a proximal end 18 of the catheter adapter 14 to activate the septum therein, thus opening a fluid path within catheter adapter 14. In some configurations, following insertion of the probe member 46 into the proximal end 22 of catheter adapter 14, conduit coupler 42 is interlock with the coupler 42 and the flange 28 (via the sets of threads 30 and 44), such as by rotation. In some embodiments, the position of probe 46 within catheter adapter 14 advances a septum activator 80 through a septum 50 of the catheter adapter 14, thereby opening a fluid pathway, as taught in U.S. patent application Ser. No. 12/544,624, which is incorporated herein by reference.

Figure 3:
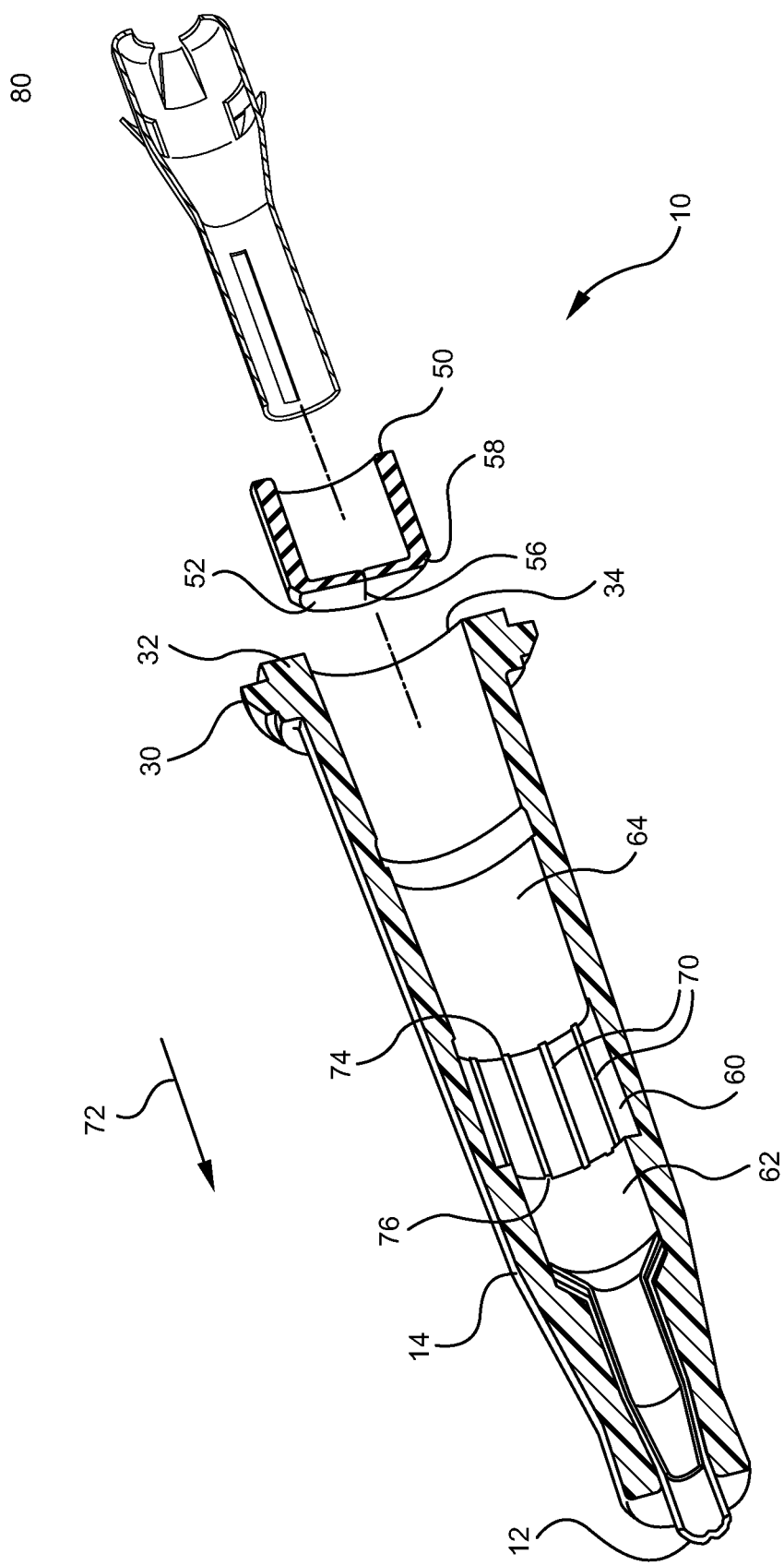
FIG. 3 is an exploded cross-sectioned view of an intravascular device in accordance with a representative embodiment of the present invention.

Referring now to FIG. 3, an exploded, cross-sectional view of an intravascular device 10 is shown. In some embodiments, intravascular device 10 comprises a catheter adapter 14 having an inner surface 60 for receiving a septum 50. In some embodiments, inner surface 60 comprises a recessed groove having a length and depth sufficient to accommodate the length and outer diameter of septum 50. Further, inner surface 60 may include one or more vents 70 which provide fluid communication between a distal chamber 62 and proximal chamber 64 of the catheter adapter 14. For example, in some embodiments vents 70 permit passage of air from distal chamber 62 to proximal chamber 64 thereby equilibrating air pressures within the adjacent chambers 62 and 64. This equilibration prevents buildup of air pressure within distal chamber 62 which may prevent a desirable flashback during insertion of catheter 12 into a patient.

In some embodiments, the one or more vents 70 are designed to allow the flow of air and stop the flow of blood. In some embodiments septum 50 comprises a single vent. In other embodiments septum 50 comprises a plurality of vents. For example, in some embodiments septum 50 comprises between two vents and forty vents. Further, in some embodiments septum 50 comprises six vents.

In some embodiments, vents 70 further comprise a proximal opening 74 and a distal opening 76. A cross sectional area of proximal and distal openings 74 and 76 may be selected to permit or exclude passage of air and/or liquid through vents 70. Accordingly, in some embodiments proximal and distal openings 74 and 76 comprise a cross sectional area between about 0.000007 to 0.00004 inches$^2$. In other embodiments, the openings 74 and 76 have a cross sectional area between about 0.00001 to 0.00003 inches$^2$. In other embodiments, openings 74 and 76 have a cross sectional area of about 0.00002 inches$^2$. For instance, in some embodiments openings 74 and 76 have a height of approximately 0.001 to 0.003 inches and a width of approximately 0.010 inches. In other embodiments, openings 74 and 76 have a height of about 0.002 to 0.003 inches and a width of about 0.005 inches.

Similarly, vents 70 between the septum 50 and the inner surface 60 of the catheter adapter 14 can be specifically configured to permit blood and air to pass therethrough at an estimated range of flow rates. For instance, in some embodiments vents 70 permit blood to flow therethrough at a rate between about 10 to 200 ml/hr. In other embodiments, vents 70 permit blood to flow therethrough at a rate between about 15 to 150 ml/hr. In yet other instances, vents 70 permit blood to flow therethrough at a rate between about 50 to 100 ml/hr. At these rates, the rate of blood flow into the proximal chamber 64 can be paced to provide a clinician with adequate time to correctly locate the catheter within a patient's blood vessel. Accordingly, in some embodiments, vents 70 have a cross sectional area greater than 0.00003 inches$^2$. In other embodiments, the vents 70 have a cross sectional area greater than 0.00004 inches$^2$. In other embodiments, the vents 70 have a cross sectional area of about 0.0001 inches$^2$. In other embodiments, the vents 70 have a cross sectional area of about 0.001 inches$^2$.

With continued reference to FIG. 3, in some embodiments septum 50 comprises a membrane 52 which provides a defeatable barrier between distal and proximal chambers 62 and 64. For example, in some embodiments membrane 52 comprises a slit 56 which is biased closed due to axial, compressive forces applied to the outer surface of septum 50 when fit into inner surface 60. In other embodiments, membrane 52 comprises a pierceable surface that may be defeated by a sharpened instrument, such as a needle tip.

Generally, septum 50 comprises a hyperelastic material that, when assembled, interfaces with inner surface 60 through interference fit. In some instances, the compressive forces experience by septum 50 in the assembly intravascular device 10 cause the cross sectional area of vents 70 and openings 74 and 76 to be deformed, wherein a portion of the septum 50 is forced into the adjacent vents 70. Accordingly, in some embodiments intravascular device 10 comprises various compression relief features to compensate for compressive forces experience due to the interference fit.

Figure 4:
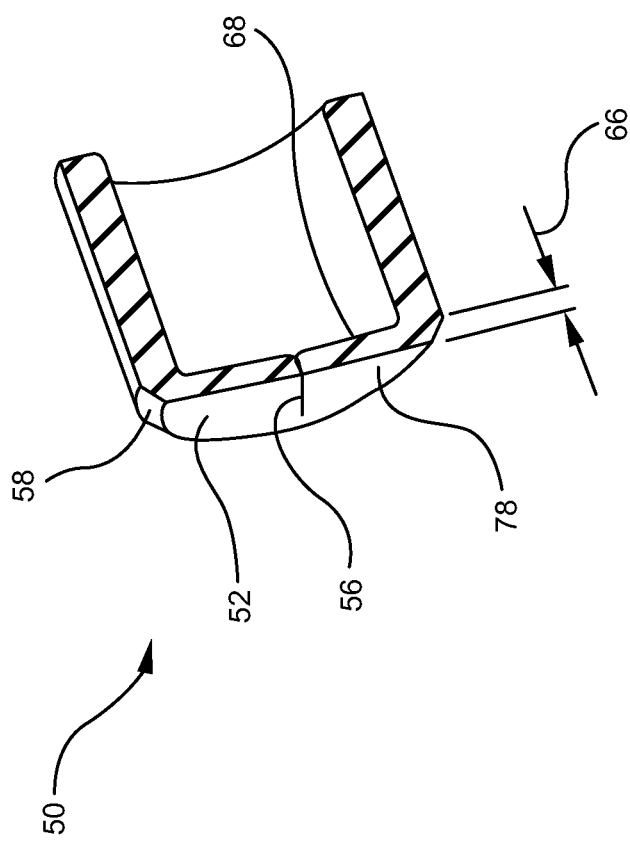
FIG. 4 is a perspective cross-sectioned view of a compression compensating septum in accordance with a representative embodiment of the present invention.
Figure 5:
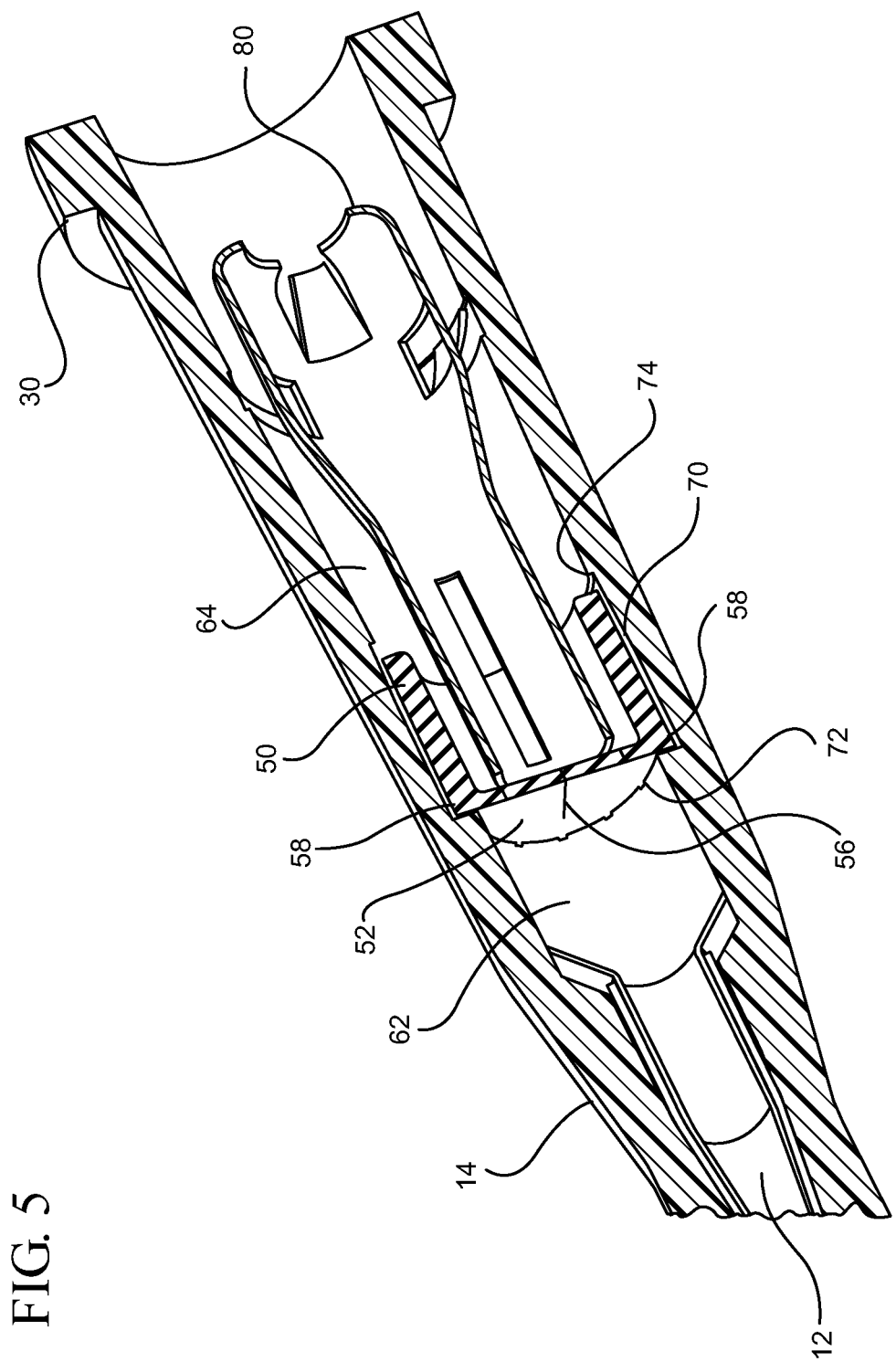
FIG. 5 is a perspective cross-sectioned view of an assembled intravascular device incorporating compression relief features in accordance with a representative embodiment of the present invention.
Figure 6:
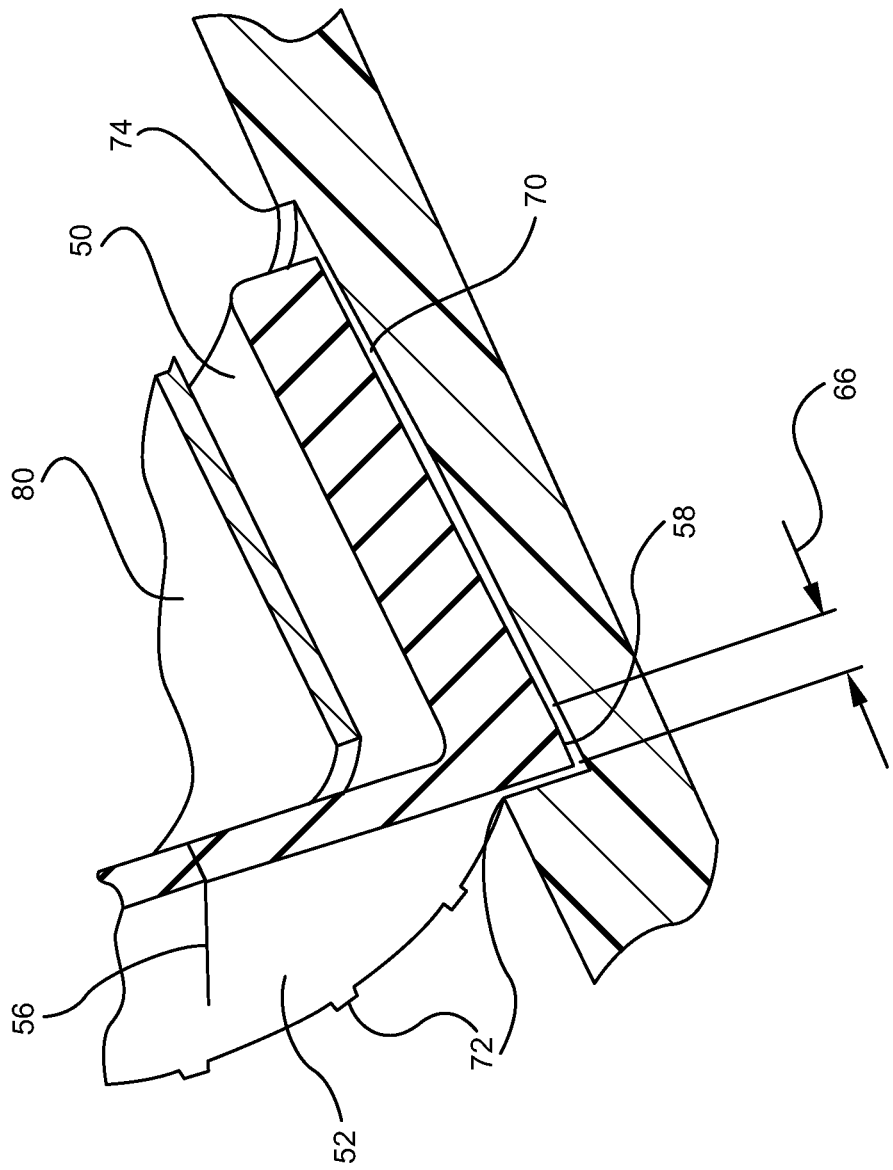
FIG. 6 is a detailed perspective cross-sectioned view of FIG. 5 in accordance with a representative embodiment of the present invention.

Referring now to FIGS. 3 and 4, in some embodiments a distal portion of septum 50 is modified to compensate for the aforementioned deformation due to compressive forces. For example, in some embodiments a chamfer 58 is provided on the distal end of the outer surface of septum 50. In some embodiments, chamfer 58 tapers inwardly in a distal direction 72, wherein the length of chamfer 58 corresponds approximately to the thickness 66 of membrane 52. In other words, in some embodiments chamfer 58 tapers inwardly from a proximal surface 68 of membrane 52 to a distal surface 78 of membrane 52. Further, in some embodiments a radial distance of chamfer 58 is approximately equal to the maximum deformation of vents 70 under maximum expected compression when assembled. As such, the vent geometry will experience minimal effect from compression, as shown in FIGS. 5 and 6.

Figure 7:
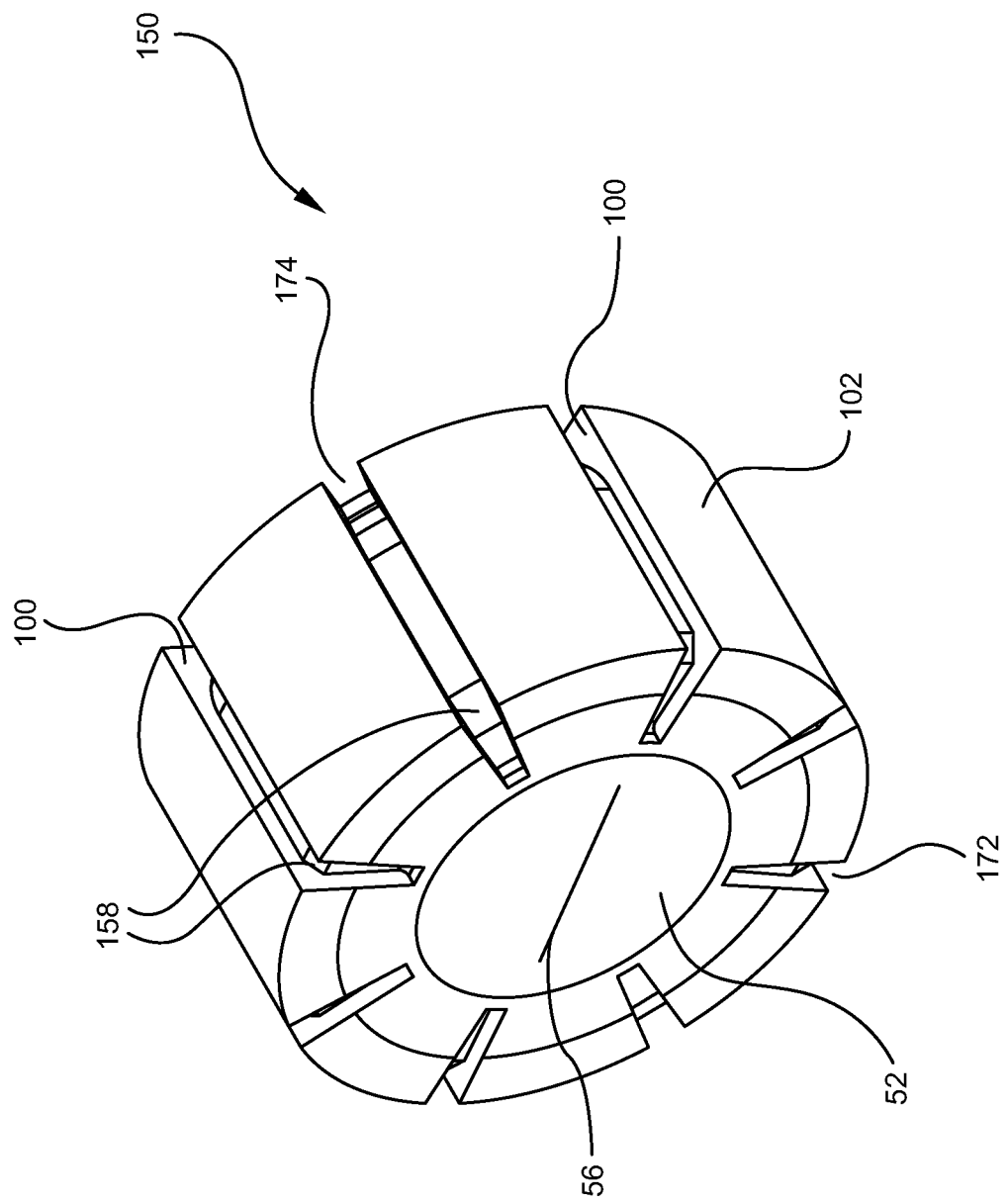
FIG. 7 is a perspective view of a septum having compression relief features in accordance with a representative embodiment of the present invention.

Referring now to FIG. 7, in some embodiments a plurality of channels or vents 100 are provided in outer surface 102 of septum 150. Thus, septum 150 may be positioned or seated within a catheter adapter 140 having a smooth inner surface 120 which does not include channels or vents, as shown in FIGS. 8B and 9A-10C, below. Thus, vent 100 provides fluid communication between distal and proximal chambers 62 and 64, in accordance with the previous discussion. Further, vents 100 comprise distal and proximal openings 172 and 174 having respective surface areas for accommodating passage of fluids, as previously discussed.

Figure 8A:
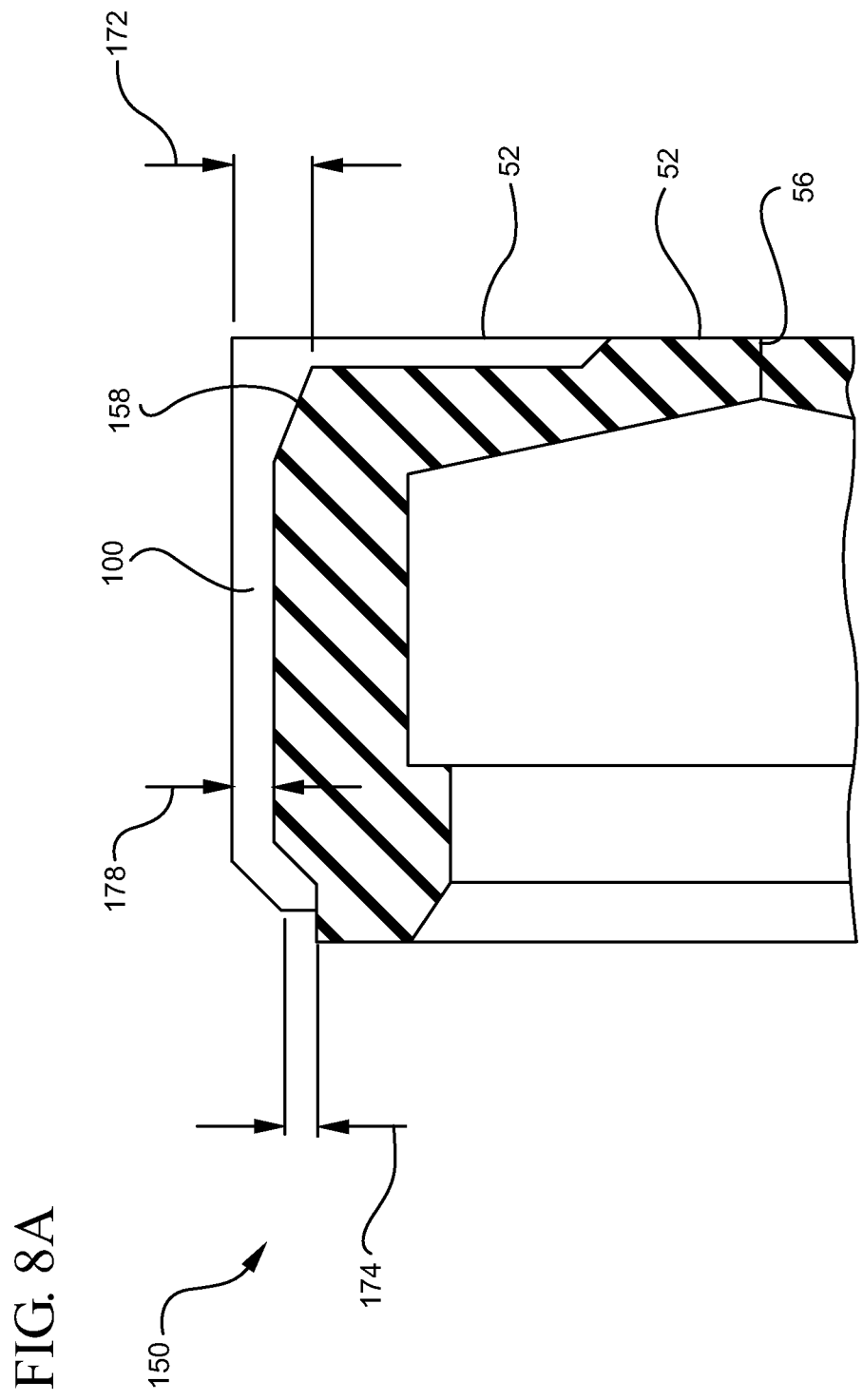
FIG. 8A is a cross-section view of the septum of FIG. 7 in accordance with a representative embodiment of the present invention.
Figure 8B:
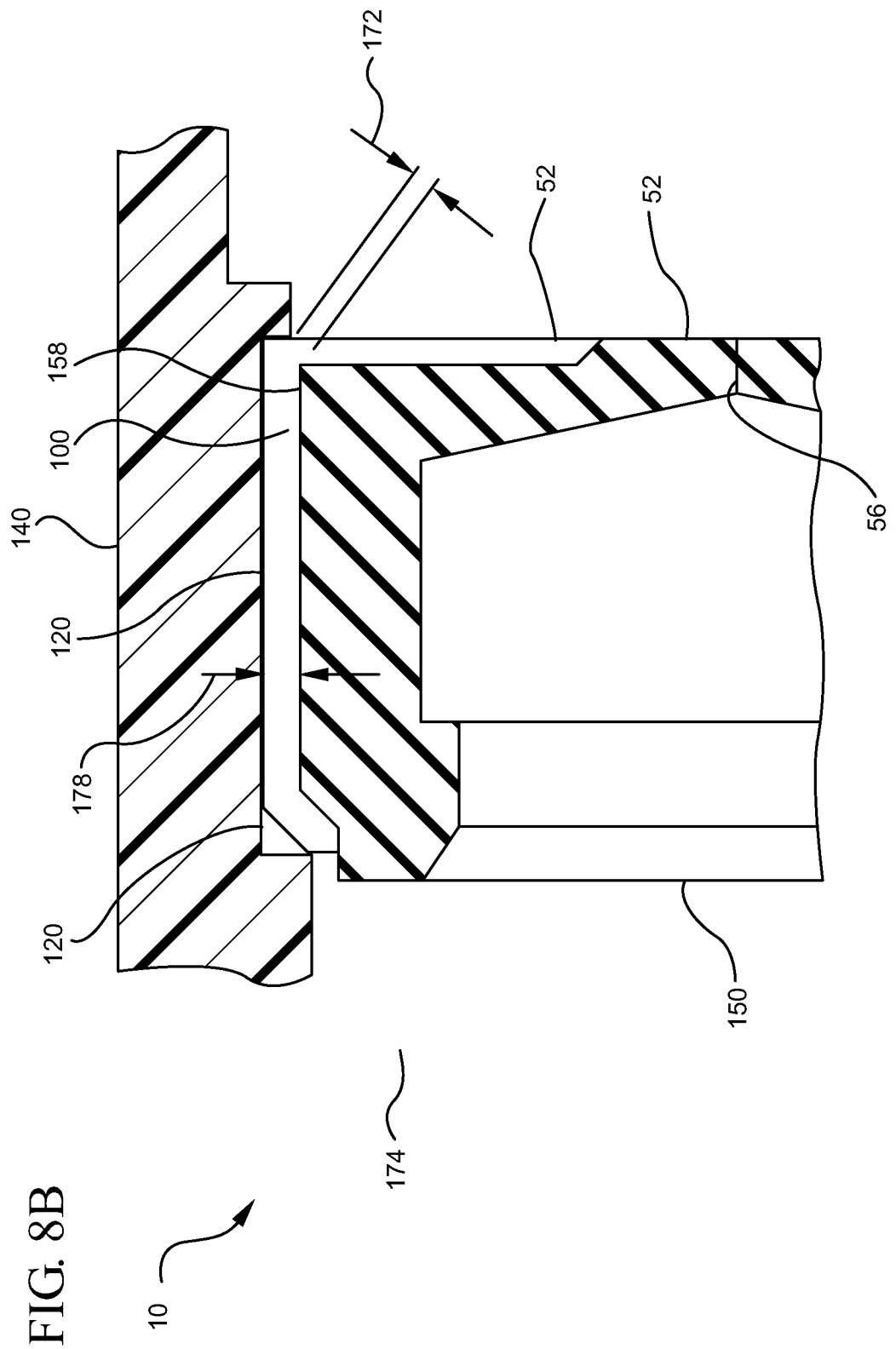
FIG. 8B is a cross-section view of FIG. 8A following assembly of an intravascular device in accordance with a representative embodiment of the present invention.

In some embodiments, a distal portion of vent 100 is chamfered 158 to compensate for the aforementioned deformation due to compressive forces of the interference fit. As shown in FIG. 8A, prior to assembly chamfer 158 provides an increased distal opening 172 which tapers outwardly in a proximal direction to a final vent depth 178. In some embodiments, compressive forces experienced at the proximal end of septum 150 are less than compressive forces experienced at the distal end of septum 150. Accordingly, in some embodiments proximal opening 174 is configured to have a cross section surface area approximately equal to the cross section surface area of vent 100 at vent depth 178. Thus, desirable final geometries of vent depth 178, distal opening 172 and proximal opening 174 are achieved following assembly of intravascular device 10, as shown in FIG. 8B.

Figure 9A:
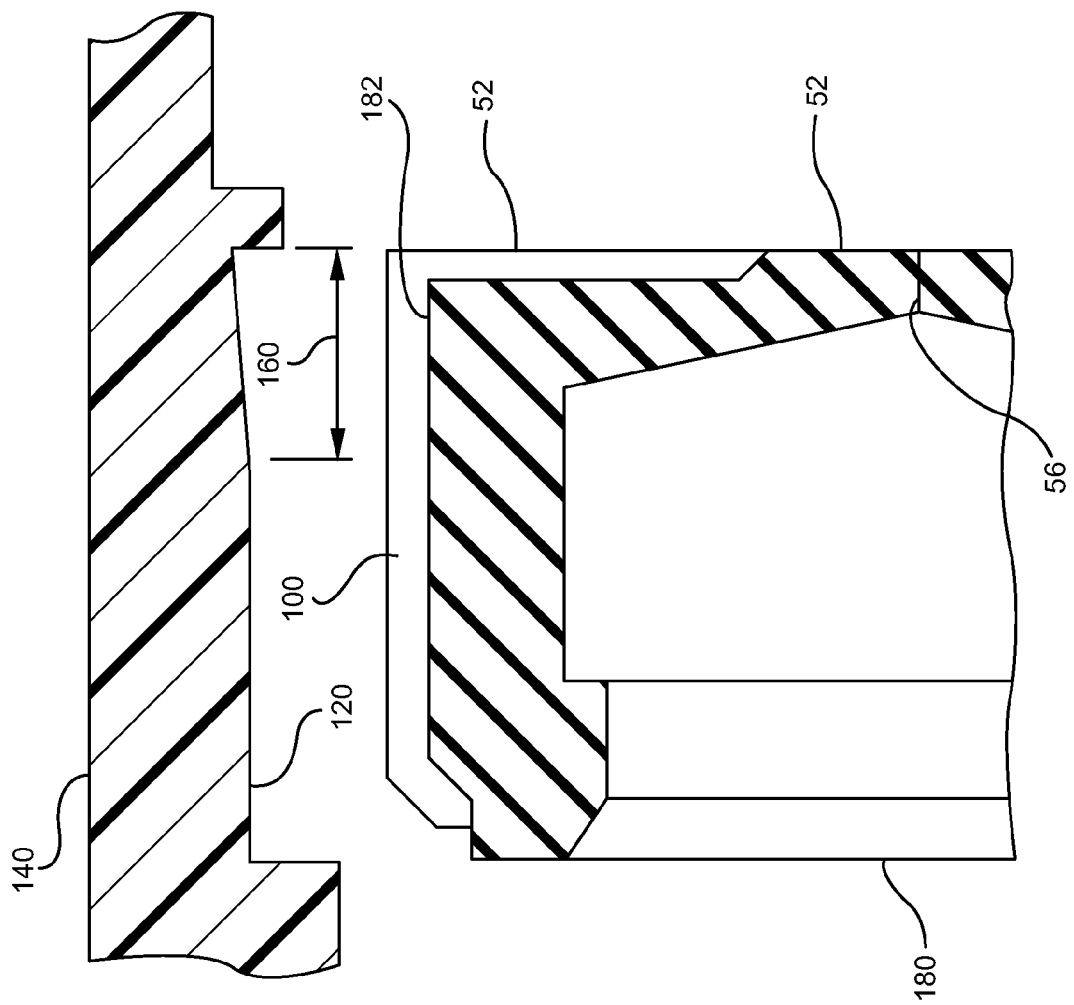
FIG. 9A is a cross-section view of a catheter adapter having compression relief features and a septum in accordance with a representative embodiment of the present invention.
Figure 9B:
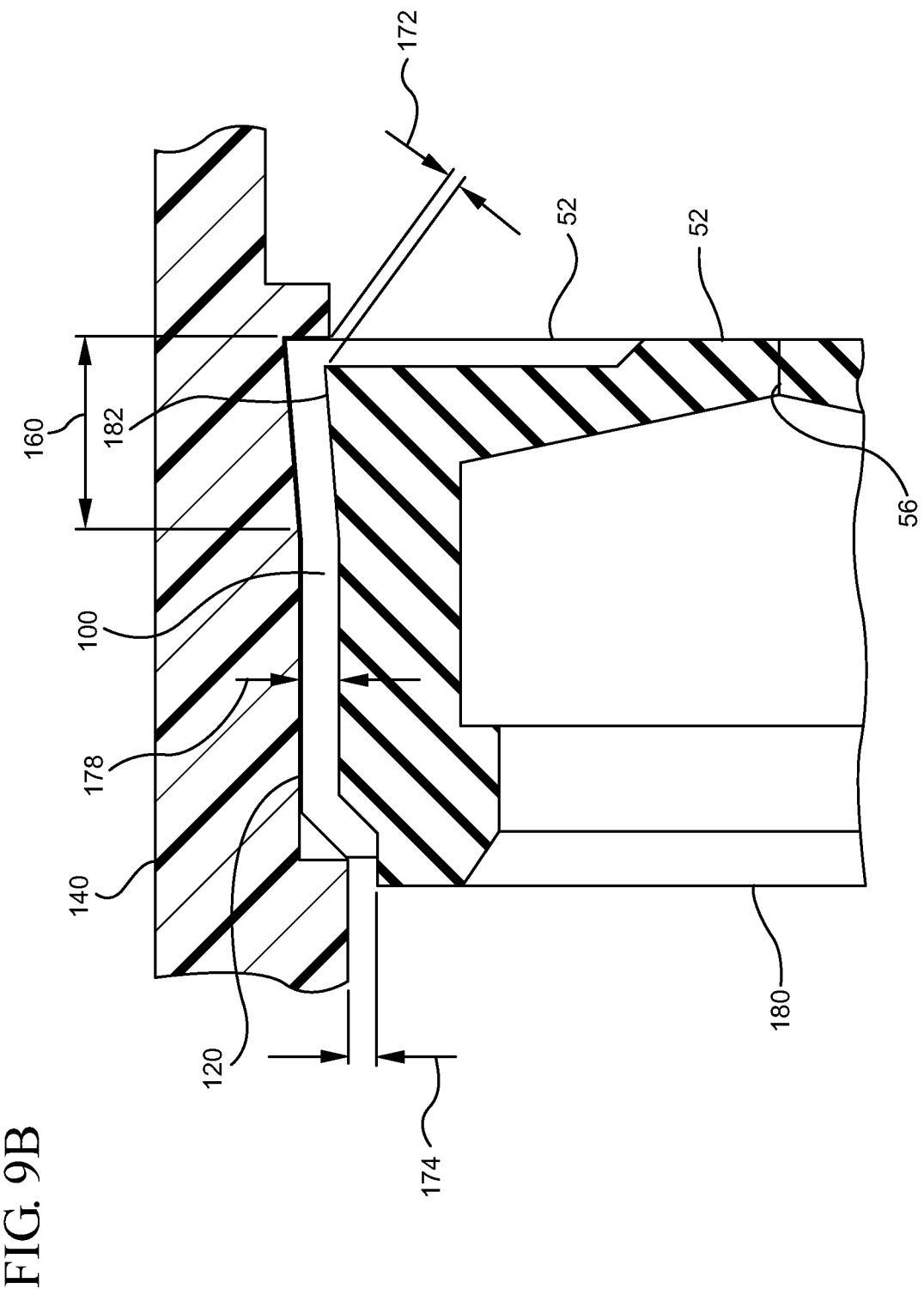
FIG. 9B is a cross-section view of the catheter adapter of FIG. 9A fitted with a septum in accordance with a representative embodiment of the present invention.

Referring now to FIG. 9A, in some embodiments a distal portion 160 of inner surface 120 is chamfered. As such, catheter adapter 140 may be used with a septum 180 having a non-chamfered distal outer surface 182, as shown. Upon assembly, surface 182 is deformed due to compressive forces, thereby causes outer surface 182 to be displaced into the chamfered portion 160 of inner surface 120, as shown in FIG. 9B. As such, the desirable final geometries of vent depth 178, distal opening 172 and proximal opening 174 are achieved.

Figure 10B:
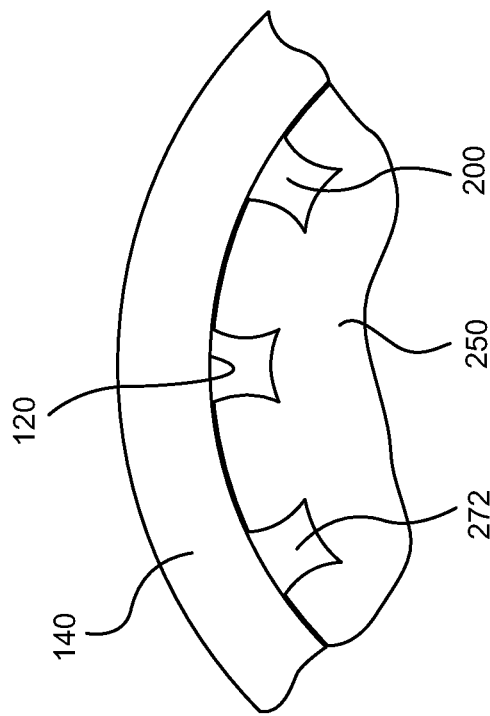
FIG. 10B is a perspective view of the distal end of a septum having compression relief features as installed in a catheter adapter of an intravascular device in accordance with a representative embodiment of the present invention.
Figure 10A:
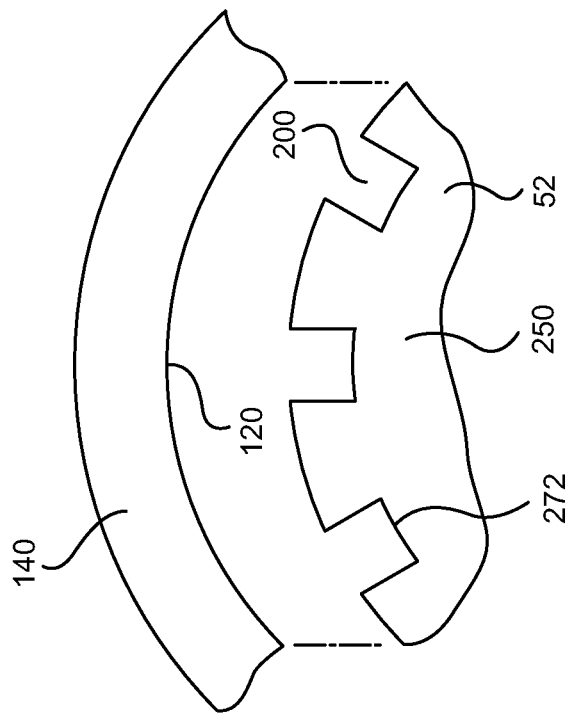
FIG. 10A is a perspective view of the distal end of a septum having compression relief features prior to being assembled in accordance with a representative embodiment of the present invention.
Figure 10C:
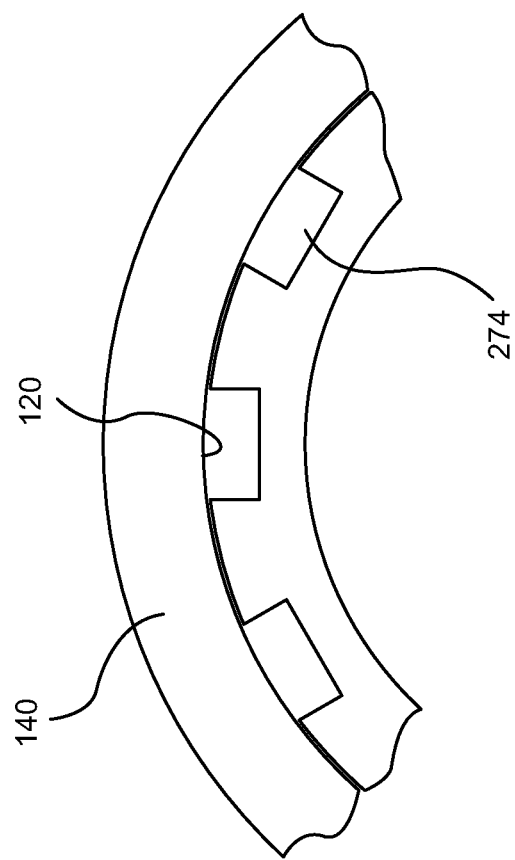
FIG. 10C is a perspective view of the proximal end of a septum having compression relief features as installed in a catheter adapter of an intravenous device in accordance with a representative embodiment of the present invention.

In some embodiments, septum 250 comprises vent 200 having a distal opening 272 with an initial cross section area that is greater than the desired final cross section area. Once assembled, compressive forces reduce the cross section area of opening 272, thereby achieving a desired final cross section area, as shown in FIG. 10B. Further, in some embodiments the desired final cross section area of distal opening 272 is equal to, or approximately equal to a desired final cross section area of the proximal opening 274, as shown in FIG. 10C. Accordingly, the compression relief features of the present invention compensate for compression forces thereby preventing occlusion or blockage of flow through the respective openings and vents.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A septum for use within an intravascular device, the intravascular device having an inner surface in which one or more vents are formed, the septum being configured to prevent an outer surface of the septum from extending into the one or more vents when the septum is compressed within the intravascular device, the septum comprising:

a cylindrical body having an outer surface, a proximal end, and a distal end forming a distal surface, the length of the cylindrical body being less than the length of the one or more vents formed in the inner surface of the intravascular device such that when the septum is placed within the intravascular device, the one or more vents extend past the distal and proximal ends of the septum to allow air or liquid to bypass the septum via the one or more vents;

wherein the outer surface has a first diameter when uncompressed and the distal surface has a second diameter less than the first diameter such that the distal end of the cylindrical body is chamfered between the outer surface and the distal surface when the septum is uncompressed, and wherein when the septum is inserted into the intravascular device, the outer surface is compressed towards the second diameter such that the distal end is not chamfered.

2. The device of claim 1, wherein the cross-section area of one or more of a proximal or distal opening of the one or more vents is from approximately 0.000007 inches$^2$ to approximately 0.00004 inches$^2$.

3. The device of claim 1, wherein the distal surface comprises a membrane having a thickness such that a proximal surface of the membrane is at a first distance relative to the distal surface, and wherein the chamfer commences at the first distance.

4. The device of claim 3, further comprising an opening forming a pathway through the membrane.

5. A septum for use within an intravascular device, the septum comprising:

a cylindrical body having an outer surface, a proximal end, and a distal end forming a distal surface, the outer surface having one or more vents that each extend from the proximal end to the distal end to thereby allow air or liquid to bypass the septum by passing through the one or more vents;

wherein each vent comprises a vent outer surface that is recessed from the outer surface of the cylindrical body and a vent distal surface that is recessed from the distal end of the cylindrical body, the vent outer surface being positioned at a first radial distance from a longitudinal axis of the septum when the septum is uncompressed and the vent distal surface extending radially to a second radial distance less than the first radial distance such that the distal end of the vent outer surface is chamfered when the septum is uncompressed, and wherein when the septum is inserted into an intravascular device, the compression of the outer surface of the cylindrical body causes the vent outer surface to be compressed towards the second radial distance such that the distal end of the vent outer surface is not chamfered.

6. The septum of claim 5, wherein a cross-sectional area of a proximal opening of each vent is approximately equal to the cross-sectional area of the vent when the septum is uncompressed.

7. The septum of claim 5, wherein a cross-sectional area of one or more of a proximal or distal opening of the one or more vents is from approximately 0.000007 inches$^2$ to approximately 0.00004 inches$^2$.

8. The septum of claim 5, wherein a cross-sectional area of each vent when the septum is uncompressed is greater than a cross-sectional area of the vent when the septum is compressed.

9. The septum of claim 5, wherein the one or more vents comprise a plurality of vents.

10. The septum of claim 9, wherein the plurality of vents are equally spaced around the outer surface of the septum.

* * * * *